United States Patent
Geers et al.

(10) Patent No.: US 8,030,359 B2
(45) Date of Patent: Oct. 4, 2011

(54) POLYMER FORMULATIONS OF CETP INHIBITORS

(75) Inventors: Sarah Geers, Weehawken, NJ (US);
Michael Lowinger, Norristown, PA (US); Craig A. McKelvey, Ambler, PA (US); Robert F. Meyer, Royersford, PA (US); Dina Zhang, Watchung, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 405 days.

(21) Appl. No.: 12/223,272

(22) PCT Filed: Feb. 9, 2007

(86) PCT No.: PCT/US2007/003799
§ 371 (c)(1),
(2), (4) Date: Jul. 24, 2008

(87) PCT Pub. No.: WO2007/092642
PCT Pub. Date: Aug. 16, 2007

(65) Prior Publication Data
US 2010/0227903 A1    Sep. 9, 2010

Related U.S. Application Data

(60) Provisional application No. 60/771,782, filed on Feb. 9, 2006.

(51) Int. Cl.
*A01N 33/18* (2006.01)
*A01N 29/10* (2006.01)
*A61K 31/12* (2006.01)

(52) U.S. Cl. .......... 514/676; 514/754; 514/684

(58) Field of Classification Search ............ None
See application file for complete search history.

(56) References Cited

U.S. PATENT DOCUMENTS

| | | |
|---|---|---|
| 6,627,767 B2 | 9/2003 | Liu et al. |
| 2002/0103225 A1 * | 8/2002 | Curatolo et al. ........ 514/313 |
| 2003/0072801 A1 | 4/2003 | Curatolo et al. |
| 2003/0104063 A1 | 6/2003 | Babcock et al. |
| 2003/0185893 A1 | 10/2003 | Beyerinck et al. |
| 2004/0225018 A1 | 11/2004 | Sunami et al. |
| 2005/0059810 A1 | 3/2005 | Maeda et al. |
| 2006/0040999 A1 | 2/2006 | Ali et al. |
| 2007/0243257 A1 * | 10/2007 | Bedos et al. ........ 424/486 |

FOREIGN PATENT DOCUMENTS

| | | |
|---|---|---|
| LB | 7254 | 1/2006 |
| WO | WO03/064376 | 7/2003 |
| WO | WO2004/092136 | 10/2004 |
| WO | WO 2007/005572 A1 * | 6/2005 |
| WO | WO 2006/014357 | 2/2006 |
| WO | WO 2007/005572 | 1/2007 |
| WO | WO 2007/067593 | 6/2007 |

OTHER PUBLICATIONS

Nan-Horng Lin et al. "Synthesis and biological evaluation of 1-benzyl-5-(3-biphenyl-2-yl-propyl)-1H-imidazole as novel farnesyltransferase inhibitor"; Bioorganic & Medicinal Chemistry Letters, Pergamon, Elsevier Science, GB; vol. 14, No. 20, Oct. 18, 2004 pp. 5057-5062 XP004565431; Compounds 20, 21.

* cited by examiner

*Primary Examiner* — Sreeni Padmanabhan
*Assistant Examiner* — Svetlana M Ivanova
(74) *Attorney, Agent, or Firm* — James L. McGinnis; Catherine D. Fitch; Mark R. Daniel

(57) ABSTRACT

A pharmaceutical composition comprises (a) a CETP inhibiting compound, or a pharmaceutically acceptable salt thereof; (b) a concentration-enhancing polymer, and (c) optionally one or more surfactants; wherein the compound has the structure shown as Formula I below. The composition raises HDL-cholesterol and lowers LDL-cholesterol.

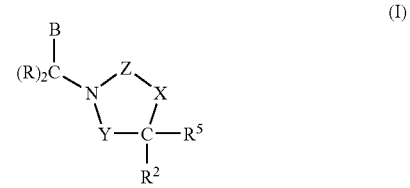

15 Claims, No Drawings

POLYMER FORMULATIONS OF CETP INHIBITORS

CROSS REFERENCE TO RELATED APPLICATIONS

This application is a U.S. National Phase application under 35 U.S.C. §371 of PCT Application No. PCT/US2007/003799, filed Feb. 9, 2007, which claims priority under 35 U.S.C. §119(e) from U.S. Application No. 60/771,782, filed Feb. 9, 2006.

FIELD OF THE INVENTION

This invention relates to solid formulations of a class of CETP inhibiting compounds which provide improved bioavailability when they are administered to a patient.

BACKGROUND OF THE INVENTION

Atherosclerosis and its clinical consequences, coronary heart disease (CHD), stroke and peripheral vascular disease, represents a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as the average age of the population increases and as an epidemic in obesity and diabetes continues to grow.

Inhibition of cholesteryl ester transfer protein (CETP) is a promising new approach to reducing the incidence of atherosclerosis. Statins have been important in reducing the incidence of CHD by reducing LDL-cholesterol (the "bad cholesterol"), but are relatively ineffective at raising HDL-cholesterol ("the good cholesterol"). CETP inhibitors raise HDL-cholesterol and may also lower-LDL-cholesterol, and may therefore provide a potent new tool for reducing CHD and atherosclerosis in the general population. Combination therapy using CETP inhibitors and statins may also become a valuable tool for controlling both HDL and LDL levels, which may make it possible to both treat and prevent atherosclerosis, and perhaps even to reverse the formation of atherosclerotic plaques. Pfizer's torcetrapib was withdrawn from Phase III clinical trials because it showed an increase in mortality in the group taking the drug compared with the control group in a long-term outcomes study. The cause of the increased mortality has not yet been determined, and the mechanism has so far not been blamed for the increase in mortality.

CETP inhibitors in general are very lipophilic. The compounds are generally nearly insoluble in water and in aqueous bodily fluids. Bioavailability of CETP inhibitors using conventional tablet formulations often is poor. Oral formulations therefore need to be developed that will make the compounds more readily bioavailable when they are administered to a patient. Furthermore, many conventional formulations comprising highly insoluble lipophilic compounds, such as the CETP inhibitors used herein, show a significant "food effect," where there is a large difference in the amount and rate of absorption into the body depending on when the patient was last fed before oral administration of the drug and whether the patient takes the drug with a meal. In general, a significant difference is observed in absorption after oral administration depending on whether the patient is in a fasted state and also on when and what the patient has eaten if the patient is not in a fasted state. Several approaches to improving bioavailability have been proposed in the patent and non-patent literature. These approaches include emulsions, microemulsions, emulsion and microemulsion preconcentrates, also known as self-emulsifying drug delivery systems (SEDD's) and self-microemulsifying drug delivery systems (SMEDD's), nanoparticles, and amorphous dispersions in a carrier. Solid formulations which are amorphous dispersions of a particularly potent class of CETP inhibitors in which the compound is dissolved or dispersed in a polymer in a non-crystalline state are described herein.

SUMMARY OF THE INVENTION

The present invention provides an orally bioavailable solid formulation of the following class of CETP inhibitors, including pharmaceutically acceptable salts, represented by Formula I:

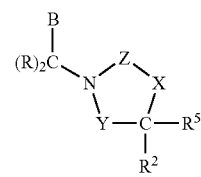

The solid formulations of this invention comprise:
(1) The active compound having formulae I-Ij and II, described above and also hereafter in this application, or a pharmaceutically acceptable salt thereof;
(2) a concentration-enhancing polymer, where the polymer increases the bioavailability of the active drug, and is water soluble or readily disperses in water, such as for example hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, polyvinylpyrrolidinone, vinyl pyrrolidinone/vinyl acetate copolymers, and acrylate and methacrylate copolymers; and
(3) optionally one or more surfactants, which may be ionic or nonionic surfactants.

In the compounds of Formula I,
Y is selected from —C(=O)— and —(CRR$^1$)—;
X is selected from —O—, —NH—, —N(C$_1$-C$_5$alkyl)-, and —(CRR$^6$)—;
Z is selected from —C(=O)—, —S(O)$_2$—, and —C(=N—R$^9$)—, wherein R$^9$ is selected from the group consisting of H, —CN, and —C$_1$-C$_5$alkyl optionally substituted with 1-11 halogens;
Each R is independently selected from the group consisting of H, —C$_1$-C$_5$ alkyl, and halogen, wherein —C$_1$-C$_5$ alkyl is optionally substituted with 1-11 halogens;
B is selected from the group consisting of A$^1$ and A$^2$, wherein A$^1$ has the structure:

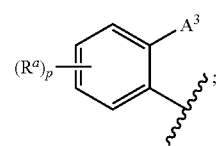

$R^1$ and $R^6$ are each independently selected from H, —$C_1$-$C_5$ alkyl, halogen, and —$(C(R)_2)_nA^2$, wherein —$C_1$-$C_5$ alkyl is optionally substituted with 1-11 halogens;

$R^2$ is selected from the group consisting of H, —$C_1$-$C_5$ alkyl, halogen, $A^1$, and —$(C(R)_2)_nA^2$, wherein —$C_1$-$C_5$ alkyl is optionally substituted with 1-11 halogens;

Wherein one of B and $R^2$ is $A^1$; and one of B, $R^1$, $R^2$, and $R^6$ is $A^2$ or —$(C(R)_2)_nA^2$; so that the compound of Formula I comprises one group $A^1$ and one group $A^2$;

$A^3$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group, wherein the point of attachment of $A^3$ to the phenyl ring to which $A^3$ is attached is a carbon atom; and
(d) a benzoheterocyclic ring comprising a phenyl ring fused to a 5-6-membered heterocyclic ring having 1-2 heteroatoms independently selected from O, N, and S, and optionally also having 1-2 double bonds (in addition to the double bond of the fused phenyl ring) wherein the point of attachment of $A^3$ to the phenyl ring to which $A^3$ is attached is a carbon atom;

$A^2$ is selected from the group consisting of
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, O, and —N(O)—, and optionally also comprising 1-3 double bonds and a carbonyl group;
(d) a benzoheterocyclic ring comprising a phenyl ring fused to a 5-6-membered heterocyclic ring having 1-2 heteroatoms independently selected from O, N, and S, and optionally also having 1-2 double bonds (in addition to the double bond of the fused phenyl ring); and
(e) a —$C_3$-$C_8$ cycloalkyl ring optionally having 1-3 double bonds;

wherein $A^3$ and $A^2$ are each optionally substituted with 1-5 substituent groups independently selected from $R^a$;

Each $R^a$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_9$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)S$C_1$-$C_6$alkyl, —OH, —$NR^3R^4$, —C(=O)$NR^3R^4$, —$NR^3$C(=O)$OC_1$-$C_6$ alkyl, —$NR^3$C(=O)$NR^3R^4$, —S(O)$_xC_1$-$C_6$ alkyl, —S(O)$_yNR^3R^4$, —$NR^3$S(O)$_yNR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$ is attached is a carbon atom, wherein said heterocyclic ring is optionally substituted with 1-5 substituent groups independently selected from halogen, —$C_1$-$C_3$ alkyl, and —$OC_1$-$C_3$ alkyl, wherein —$C_1$-$C_3$ alkyl and —$OC_1$-$C_3$ alkyl are optionally substituted with 1-7 halogens;

wherein for compounds in which $R^a$ is selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —$CO_2C_1$-$C_6$alkyl, —C(=O)S$C_1$-$C_6$alkyl, —$NR^3$C(=O)$OC_1$-$C_6$ alkyl, and —S(O)$_xC_1$-$C_6$ alkyl, $R^a$ is optionally substituted with 1-15 halogens and is optionally also substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —$OC_1$-$C_4$alkyl optionally substituted with 1-9 halogens and optionally also substituted with 1-2 substituent groups independently selected from —$OC_1$-$C_2$ alkyl and phenyl, (f) —$OC_3$-$C_8$ cycloalkyl optionally having 1-3 double bonds and optionally substituted with 1-15 halogens, (g) —$CO_2$H, (h) —C(=O)$CH_3$, (i) —$CO_2C_1$-$C_4$alkyl which is optionally substituted with 1-9 halogens, and (j) phenyl which is optionally substituted with 1-3 groups independently selected from halogen, —$CH_3$, —$CF_3$, —$OCH_3$, and —$OCF_3$;

with the proviso that when B is $A^1$, and X and Y are —$CH_2$—, and Z is —C(=O)—, and $R^2$ is phenyl which has a substituent $R^a$ in the 4-position, wherein $R^a$ is —$OC_1$-$C_6$alkyl which is optionally substituted as described above, then there are no other $R^a$ substitutents on $R^2$ in which $R^a$ is selected from —OH, —$OC_1$-$C_6$alkyl, —$OC_2$-$C_6$ alkenyl, —$OC_2$-$C_6$ alkynyl, and —$OC_3$-$C_8$ cycloalkyl optionally having 1-3 double bonds, all of which are optionally substituted as described above;

n is 0 or 1;
p is an integer from 0-4;
x is 0, 1, or 2;
y is 1 or 2;

$R^3$ and $R^4$ are each independently selected from H, —$C_1$-$C_5$ alkyl, —C(=O)$C_1$-$C_5$ alkyl and —S(O)$_yC_1$-$C_5$ alkyl, wherein —$C_1$-$C_5$ alkyl in all instances is optionally substituted with 1-11 halogens; and $R^5$ is selected from the group consisting of H, —OH, —$C_1$-$C_5$ alkyl, and halogen, wherein —$C_1$-$C_5$ alkyl is optionally substituted with 1-11 halogens.

In the compounds of Formula I and in subsequent groups of compounds, alkyl, alkenyl, and alkynyl groups can be either linear or branched, unless otherwise stated.

DETAILED DESCRIPTION OF THE INVENTION

Concentration-enhancing polymers are polymers that form amorphous dispersions with active pharmaceutical ingredients (API's) that are insoluble or almost completely insoluble in water by (a) dissolving the API or (b) interacting with the API in such a way that the API does not form crystals or crystalline domains in the polymer. The concentration-enhancing polymers are water soluble or readily disperse in water, so that when the polymer is placed in water or an aqueous environment (eg. fluids in the gastrointestinal (GI) tract or simulated GI fluids), the solubility and/or bioavailability of the API is increased over the solubility or bioavailability in the absence of the polymer.

The solid dispersions are made by methods that are suitable for causing a compound (the drug) to form a dispersion (also referred to as an amorphous dispersion) in the polymer such that the drug is generally amorphous or dissolved in the polymer or a component of the composition, such as a surfactant. The dispersions are stable, and the drug does not form crystals or other insoluble particles. Such methods include solution methods, such as spray drying, spray coating, freeze-drying, and evaporation of a co-solvent under vacuum or by heating a solution of polymer and drug. Such methods also include methods that blend the solid drug with the polymer in the molten state, such as hot melt extrusion, and methods of compounding the solid non-molten polymer and drug under heat and pressure to form a dispersion.

The compositions comprising the concentration-enhancing polymer increase the concentration of the CETP inhibitor in an aqueous environment, such as water, the gastrointestinal (GI) tract, or a simulated GI fluid prepared for in vitro laboratory tests relative to a control composition comprising an equivalent amount of the CETP inhibitor without polymer. Once the composition is introduced into an aqueous environment, the composition comprising the concentration-enhancing polymer and CETP inhibitor provides a higher maximum aqueous concentration of CETP inhibitor relative to a control composition having the same concentration of CETP inhibitor but without the concentration-enhancing polymer. An inert filler may be used in place of the polymer in the control to keep the CETP inhibitor at the same concentration as in the composition comprising the polymer. The polymer preferably increases the maximum concentration of the CETP inhibitor in an aqueous solution by at least 25%, more preferably at least 50%, more preferably increases the drug concentration to at least double relative to a control composition, or increases the drug concentration to at least 5-times greater that than that of a control composition, or increases the drug concentration by at least 10-fold. Such large enhancements in concentration may be necessary in order for extremely water insoluble CETP inhibitors to achieve effective blood levels through oral dosing. Such aqueous solutions are generally supersaturated solutions with respect to the CETP inhibitor.

In in vivo pharmacokinetics measurements in which the concentration of the drug is measured as a function of time in blood or serum after administration of the formulation to a test animal, the compositions of this application exhibit a maximum concentration $C_{max}$ and an area under the concentration versus time curve (AUC) that is greater than that of a control composition comprising an equivalent quantity of the cholesteryl ester transfer protein inhibitor without the concentration-enhancing polymer. The area under the concentration versus time curve (AUC) is preferably at least 25% greater than that of a control composition, more preferably at least 50% greater than that of a control composition, more preferably the area is at least double, or at least 5-times greater, or at least 10-fold greater than that of a control composition containing the same amount of drug but without the polymer. The $C_{max}$ is also increased, preferably by at least 25%, more preferably by at least 50%, more preferably $C_{max}$ is increased to at least double relative to a control composition, or at least 5-times greater that than that of a control composition, or at least 10 times greater than the drug concentration of a control composition without the polymer after it is administered to a test animal or patient.

The compositions disclosed herein exhibit improved in vivo bioavailability of the CETP inhibitor compared with formulations that do not have the concentration-enhancing polymer. The active CETP inhibitor is absorbed more rapidly after oral administration of these formulations. The AUC of the drug and the maximal concentration of the drug in the blood or serum are increased when the formulations are administered to a patient.

Concentration-Enhancing Polymers. One class of polymers suitable for use with the present invention comprises neutral non-cellulosic polymers. Exemplary polymers include: vinyl polymers and copolymers having substituents that are hydroxy, alkyl, acyloxy, and cyclic amides. These include polyvinyl alcohols that have at least a portion of their repeat units in the unhydrolyzed (vinyl acetate) form (e.g. polyvinyl alcohol-polyvinyl acetate copolymers); polyvinyl pyrrolidinone; polyethylene polyvinyl alcohol copolymers; and polyvinylpyrrolidinone-polyvinyl acetate copolymers. A preferred class of non-cellulosic nonionic polymers comprises polyvinylpyrrolidinone and polyvinylpyrrolidinone copolymers, such as polyvinylpyrrolidinone-polyvinyl acetate copolymers, available as Kollidon polymers and copolymers. A representative copolymer is Kollidon VA64 (copovidone).

Another class of polymers suitable for use with the present invention comprises ionizable non-cellulosic polymers. Exemplary polymers include: carboxylic acid functionalized vinyl polymers, such as the carboxylic acid functionalized polymethacrylates and carboxylic acid functionalized polyacrylates, such as the EUDRAGITS copolymers, manufactured by Rohm Tech Inc., of Malden, Mass.; amine-functionalized polyacrylates and polymethacrylates; proteins; and carboxylic acid functionalized starches such as starch glycolate.

Concentration enhancing polymers may also be non-cellulosic polymers that are amphiphilic, which are copolymers of a relatively hydrophilic and a relatively hydrophobic monomer. Examples include the acrylate and methacrylate copolymers (EUDRAGITS) mentioned previously. Another example of amphiphilic polymers are block copolymers of ethylene oxide (or glycol) and propylene oxide (or glycol), where the poly(propylene glycol) oligomer units are relatively hydrophobic and the poly(ethylene glycol) units are relatively hydrophilic. These polymers are often sold under the Poloxamer trademark.

A preferred class of polymers comprises ionizable and neutral cellulosic polymers with at least one ester- and/or ether-linked substituent in which the polymer has a degree of substitution of at least 0.1 for each substituent. In the nomenclature used herein, ether-linked substituents are recited prior to "cellulose" as the moiety attached to the cellulose backbone by an ether linkage; for example, "ethylbenzoic acid cellulose" has ethoxybenzoic acid substituents on the cellulose backbone. Analogously, ester-linked substituents are recited after "cellulose" as the carboxylate; for example, "cellulose phthalate" has one carboxylic acid of each phthalate moiety ester-linked to the polymer, with the other carboxylic acid group of the phthalate group remaining as a free carboxylic acid group.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.1 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3.

Also included within each polymer family type are cellulosic polymers that have additional substituents added in relatively small amounts that do not substantially alter the performance of the polymer.

Amphiphilic cellulosics may be prepared by substituting the cellulose at any or all of the 3 hydroxyl substituents present on each saccharide repeat unit with at least one relatively hydrophobic substituent. Hydrophobic substituents may be essentially any substituent that, if substituted at a high enough level or degree of substitution, can render the cellulosic polymer essentially aqueous insoluble. Hydrophilic regions of the polymer can be either those portions that are relatively unsubstituted, since the unsubstituted hydroxyls are themselves relatively hydrophilic, or those regions that are substituted with hydrophilic substituents. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl-groups such as phenyl, benzoate, or phenylate. Hydrophilic groups include ether- or ester-linked nonionizable groups such as the hydroxyalkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary etherlinked non-ionizable substituents include: alkyl groups, such as methyl, ethyl, propyl, butyl, etc.; hydroxyalkyl groups such as hydroxymethyl, hydroxyethyl, hydroxypropyl, etc.; and aryl groups such as phenyl. Exemplary ester-linked non-ionizable groups include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid, such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as aminosalicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer water soluble at least at pH values where any ionizable groups are ionized. In some cases, the aromatic group may itself be ionizable, such as phthalate or trimellitate substituents.

Exemplary cellulosic polymers that are at least partially ionized at physiologically relevant pH's include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, and hydroxyethyl cellulose acetate succinate.

As listed above, a wide range of polymers may be used to form amorphous dispersions of CETP inhibitors. One preferred sub-group comprises cellulosic polymers that are water soluble in their nonionized state and are also water soluble in their ionized state. A particular subclass of such polymers are the so-called "enteric" polymers, which include, for example, certain grades of hydroxypropyl methyl cellulose acetate phthalate and cellulose acetate trimellitate. Dispersions formed from such polymers generally show large enhancements of the maximum drug concentration in dissolution tests relative to that for a crystalline drug control. In addition, non-enteric grades of such polymers as well as closely related cellulosic polymers are expected to perform well due to the similarities in physical properties within the CETP inhibitor class.

An especially preferred group of cellulosic polymers comprises hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate and cellulose acetate isophthalate. The most preferred polymers are hydroxypropyl methyl cellulose acetate succinate, hydroxypropyl methyl cellulose phthalate, cellulose acetate phthalate, and cellulose acetate trimellitate.

When specific polymers that are suitable for use in the compositions of the present invention are blended, the blends of such polymers may also be suitable. Thus the term "polymer" is intended to include blends of polymers in addition to a single species of polymer.

Amorphous dispersions of the CETP inhibitors of Formula I and concentration-enhancing polymer may be made according to any known process which results in at least a major portion (at least 60%, preferably at least 80%, more preferably at least 90%) of the CETP inhibitor being in the amorphous state. These include mechanical processes, such as milling and extrusion; melt processes, such as high temperature fusion, hot melt extrusion, solvent modified fusion, and melt congealing processes; and solvent processes, including non-solvent precipitation processes, spray coating, and spray-drying. Although the dispersions of the present invention may be made by any of these processes, it is generally preferred that the CETP inhibitor in the amorphous dispersions is substantially amorphous and is substantially homogeneously distributed throughout the polymer. The relative amounts of crystalline and amorphous CETP inhibitor of Formula I can be determined by several analytical methods, including differential scanning calorimetry (DSC) and x-ray powder diffraction (XRPD).

Preferred processes for making amorphous dispersions of compounds of Formula I in a concentration-enhancing polymer include (a) hot melt extrusion and (b) spray drying. Preferred polymers for use in these processes are polyvinylpyrrolidinone, polyvinylpyrrolidinone-polyvinylacetate copolymers (for example Kollidon), HPC, HPMCAS, HPMC, HPMCP, CAP, and CAT. Preferred polymers for use in hot melt extrusion are polyvinylpyrrolidinone and polyvinylpyrrolidinone-polyvinylacetate copolymers (Kollidon), with Kollidon VA64 (copovidone) being the most preferred polymer, Preferred polymers for spray drying include HPC, HPMCAS, HPMC, HPMCP, CAP, and CAT, with HPMCAS being the most preferred polymer. Both of these processes are well known in the art. In spray drying, the polymer, active compound, and other optional ingredients, such as surfactants, are dissolved in a solvent and are then sprayed through a nozzle as a fine spray into a chamber where the solvent is evaporated quickly to make fine particles comprising polymer, drug, and optional other ingredients. The solvent is any solvent in which all of the components of the composition are soluble and which is readily evaporated in a spray drier. The solvent should also be suitable for use in preparing pharmaceutical compositions. Exemplary solvents are acetone, methanol and ethanol. Methanol and acetone are preferred. In hot melt extrusion, the polymer, drug, and optional surfactants are mixed together in a wet granulation process or other mixing process, and then the mixture of polymer, drug and surfactant are fed into the chamber of an extruder, preferably a twin screw extruder to obtain better mixing, and are then thoroughly melted and mixed to make an amorphous dispersion.

The amorphous dispersions may optionally have one or more surfactants included in the formulation. The surfactants can increase the rate of dissolution by facilitating wetting, thereby increasing the maximum concentration of dissolved drug. The surfactants may also make the dispersion easier to process. Surfactants may also stabilize the amorphous dispersions by inhibiting crystallization or precipitation of the drug by interacting with the dissolved drug by such mechanisms as complexation, formation of inclusion complexes, formation of micelles, and adsorption to the surface of the solid drug. Suitable surfactants include cationic, anionic, and nonionic surfactants. These include for example fatty acids and alkyl sulfonates; cationic surfactants such as benzalkonium chloride (Hyamine 1622, available from Lonza, Inc., Fairlawn, N.J.); anionic surfactants, such as dioctyl sodium sulfosuccinate (Docusate Sodium, available from Mallinckrodt Spec. Chem., St. Louis, Mo.) and sodium lauryl sulfate (sodium dodecyl sulfate); sorbitan fatty acid esters (SPAN series of surfactants); Vitamin E TPGS; polyoxyethylene sorbitan fatty acid esters (Tween series of surfactants, available from ICI Americas Inc., Wilmington, Del.); polyoxyethylene castor oils and hydrogenated castor oils such as Cremophor RH-40 and Cremopher EL; Liposorb P-20, available from Lipochem Inc., Patterson N.J.; Capmul POE-0, available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides.

The formulations disclosed herein have utility in treating diseases that can be treated with CETP inhibitors, including atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, vascular complications of diabetes, obesity and endotoxemia, wherein each disease is treated by administering a formulation disclosed herein to a patient in need of treatment for the disease, where the formulation is administered in an amount that is therapeutic for that particular disease.

The formulations disclosed herein are also used in the manufacture of medicaments for treating the diseases described above.

In the case of certain diseases, such as atherosclerosis, peripheral vascular disease, cardiovascular disorders, ischemia, cardiac ischemia, stroke, myocardial infarction, reperfusion injury, angioplastic restenosis, and vascular complications of diabetes, the formulations may be suitable for preventing the disease or delaying the onset of the disease in patients who are at risk of developing the disease. The formulations may also be useful in preventing or delaying the recurrence of certain diseases or adverse events, such as myocardial infarction, ischemia, cardiac ischemia, and stroke.

The formulations comprising compounds having formula I-Ij and II are also useful for lowering LDL cholesterol in a patient having elevated LDL cholesterol. The formulations are also useful for raising HDL cholesterol in a patient having low HDL cholesterol. The formulations may be especially beneficial to a patient by raising both HDL cholesterol and reducing LDL cholesterol, thereby increasing the ratio of HDL:LDL cholesterol. An increase in the ratio of HDL:LDL cholesterol is generally believed to be an indicator of a reduced risk of heart attack. It has also been observed that the formulations disclosed herein do not increase blood pressure, as had occurred in some patients who were taking torcetrapib.

With respect to the class of CETP inhibitors, numerous embodiments of the compounds of formula I are described below:

In preferred subsets of compounds having formula I, X is selected from the group consisting of —O—, —NH—, and —N($C_1$-$C_3$alkyl)-. X may also be selected from the group consisting of —O—, —NH—, and —N($CH_3$). In highly preferred subsets, X is O.

In many embodiments, Z is —C(=O)—.

A preferred subgroup of compounds has Formula Ie, including pharmaceutically acceptable salts thereof

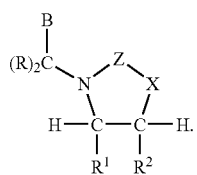

Ie

In compounds of formula Ie, X is selected from the group consisting of —O—, —NH—, —N($C_1$-$C_5$alkyl)- and —($CH_2$)—;

Z is selected from the group consisting of —C(=O)—, —S(O)$_2$—, and —C(=N—$R^9$)—, wherein $R^9$ is selected from the group consisting of H, —CN, and $C_1$-$C_5$alkyl optionally substituted with 1-11 halogens;

Each R is independently selected from the group consisting of H and —$CH_3$;

B is selected from the group consisting of $A^1$ and $A^2$, wherein $A^1$ has the structure:

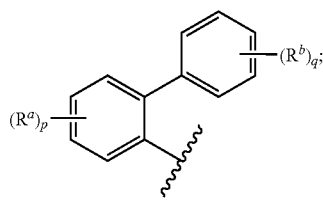

$R^1$ is selected from the group consisting of H, —$C_1$-$C_5$ alkyl, and —(C(R)$_2$)$_n$$A^2$, wherein —$C_1$-$C_5$ alkyl is optionally substituted with 1-11 halogens;

$R^2$ is selected from the group consisting of H, —$C_1$-$C_5$ alkyl, $A^1$, and —(C(R)$_2$)$_n$$A^2$, wherein —$C_1$-$C_5$alkyl is optionally substituted with 1-11 halogens;

Wherein one of B and $R^2$ is $A^1$; and one of B, $R^1$, and $R^2$ is $A^2$ or —(C(R)$_2$)$_n$$A^2$; so that the compound of Formula Ie comprises one group $A^1$ and one group $A^2$;

$A^2$ is selected from the group consisting of phenyl, cyclohexyl, and pyridyl, wherein $A^2$ is optionally substituted with 1-2 substituent groups independently selected from halogen, —$C_1$-$C_4$ alkyl, and —CN, wherein —$C_1$-$C_4$ alkyl is optionally substituted with 1-3 halogens;

Each $R^a$ is independently selected from the group consisting of —$C_1$-$C_3$ alkyl and halogen, wherein —$C_1$-$C_3$ alkyl is optionally substituted with 1-3 halogens;

Each $R^b$ is independently selected from the group consisting of Cl, F, —$C_1$-$C_4$ alkyl, and —O$C_1$-$C_4$ alkyl, wherein —$C_1$-$C_4$ alkyl and —O$C_1$-$C_4$ alkyl are optionally substituted with 1-5 F;

n is 0 or 1;
p is an integer from 0-2; and
q is an integer from 0-3.

Subsets of compounds having formula k include compounds of formula If, Ig, and Ih, and pharmaceutically acceptable salts thereof:

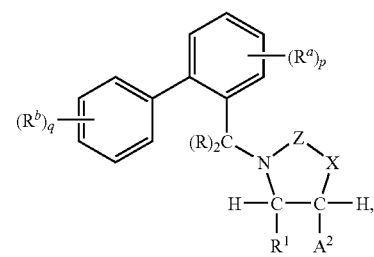

If

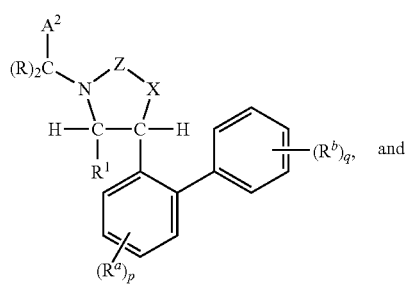

Ig and

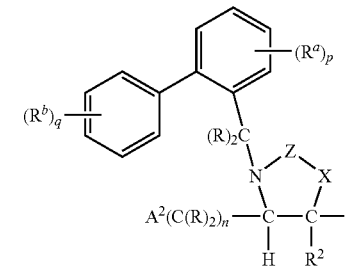

Ih

In the compounds of formula If, Ig, and Ih, $R^1$ and $R^2$ are each independently selected from H and —$C_1$-$C_5$ alkyl, wherein —$C_1$-$C_5$ alkyl is optionally substituted with 1-11 halogens. Other groups are as defined previously.

In subsets of the compounds described above, $A^2$ may be selected from the group consisting of phenyl, cyclohexyl, and pyridyl, wherein $A^2$ is optionally substituted with 1-2 substituent groups independently selected from halogen, —$CH_3$—$CF_3$, and —CN.

In subsets of the compounds described above, each $R^a$ independently is selected from the group consisting of —$CF_3$ and Cl.

In subsets of the compounds described above, each $R^b$ is independently selected from the group consisting of —$C_1$-$C_3$ alkyl, —$OCH_3$, and F.

In subsets of the compounds described above, $R^1$ and $R^2$ are each independently selected from the group consisting of H and —$C_1$-$C_2$ alkyl.

In subsets of the compounds described above, X is selected from —O—, —NH—, —N(CH$_3$)—, and —CH$_2$—.

In subsets of the compounds described above, Z is selected from the group consisting of —C(=O)—, —S(O)$_2$—, and —C(=N—CN)—.

In subsets of the compounds described above, p is 1.

In subsets of the compounds described above, q is 2 or 3.

A subset of compounds defined previously comprises compounds having formula Ii, and pharmaceutically acceptable salts thereof:

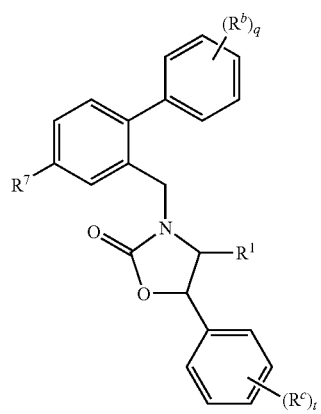

Ii

In formula Ii, $R^7$ is selected from the group consisting of Cl and —CF$_3$;

$R^c$ is selected from the group consisting of halogen, —CH$_3$—CF$_3$, and —CN; and t is an integer from 0-2. Other groups are as defined previously.

A subset of compounds defined previously comprises compounds having formula Ij, or a pharmaceutically acceptable salt thereof:

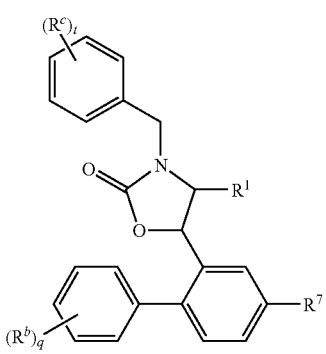

Ij

In formula Ij, $R^7$ is selected from the group consisting of Cl and —CF$_3$;

$R^c$ is selected from the group consisting of halogen, —CH$_3$—CF$_3$, and —CN; and t is an integer from 0-2. Other groups are as defined previously.

A particularly preferred embodiment of this invention is directed to the compound having formula II, including pharmaceutically acceptable salts thereof:

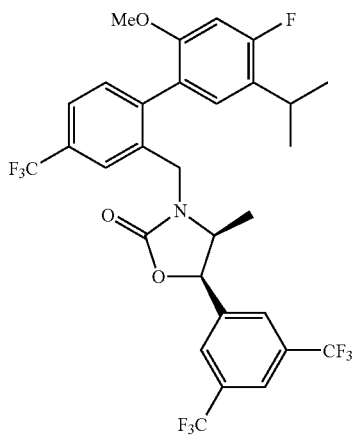

II

The class of compounds described above, including the compound having formula II, is described in commonly assigned PCT Application Nos. WO2006/014413 and WO2006/014357. Syntheses of these compounds are provided in the applications cited above. A synthesis of Compound II and related compounds is also provided below.

DEFINITIONS

The terms used throughout this application, and particularly in the examples, are generally well known to chemists who work in the area of process research and pharmaceutical research. Some of these terms are defined below:

"EDC" is 1-ethyl-3-(3-dimethylaminopropyl)carbodiimide.

"DIPEA" is diisopropylethylamine.

"Halogen" includes fluorine, chlorine, bromine and iodine.

"HOBT" is 1-Hydroxybenzotriazole.

"IPAC" is isopropyl acetate.

"Me" represents methyl.

"NaHMDS" is sodium hexamethydisilazide.

"Weinreb amine" is N,O-dimethylhydroxylamine.

Synthesis of Compound II and Related Compounds

The CETP inhibitors that are made into formulations in this application are made by a highly convergent synthesis, shown in the equation below for the compound having formula I, which is identified in the following schemes as Compound 12. The synthesis comprises the synthesis of two key intermediates, A and B. The key intermediates A and B are then coupled in an alkylation reaction of the oxazolidinone and the biphenylalkyl group substituted with Y to yield the final product 12.

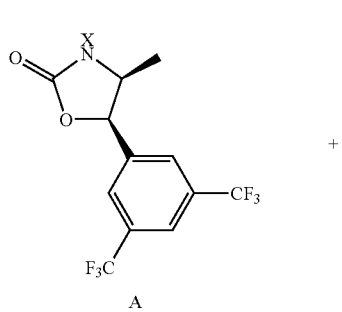

A

+

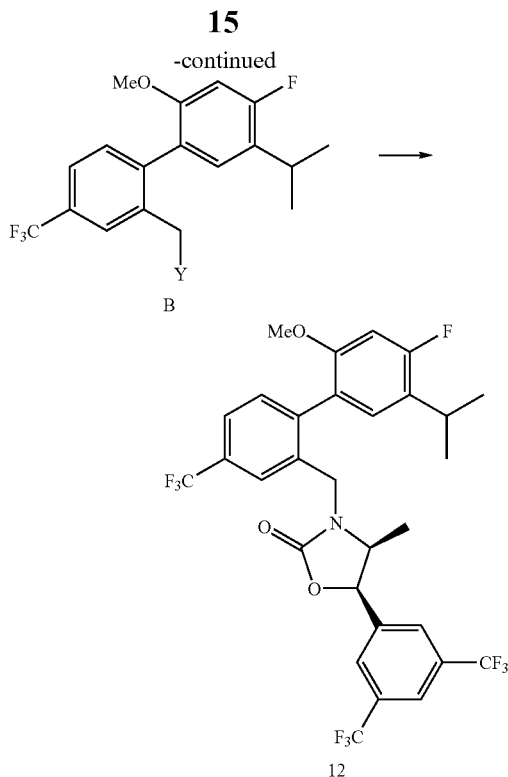

In the sequence above, in Intermediate A, X is H or the cation of a group 1 metal (e.g. Na, K, Li, or Cs) on the conjugate base of the amine, which can be obtained by reaction of a metal hydride or an alkyl metal compound with the free amine. Examples include the free oxazolidinone as the reactant (X=H), or the Na, K, Li, or Cs salt of the deprotonated oxazolidinone, as would be made by reaction of the oxazolidinone with such reagents as sodium amide, NaHMDS, or KHMDS. The preferred X groups are H and Na. The most preferred group for this particular reaction is Na.

Y is a leaving group (i.e. a group that is easily displaced). The leaving group is usually anionic after it has been displaced. The most common leaving groups are halogens, such as Cl, Br, I or F. The leaving group may also be the deprotonated form of an organic acid, such as triflate or trifluoroacetate. The most preferred leaving groups Y are the halogens Br, Cl and I. A complete synthesis of Compound 12 is shown below. Syntheses of this compound and related CETP inhibitor compounds are provided in commonly assigned PCT Application No. 2005/023775 and U.S. application Ser. No. 11/173,295.

SCHEME 1

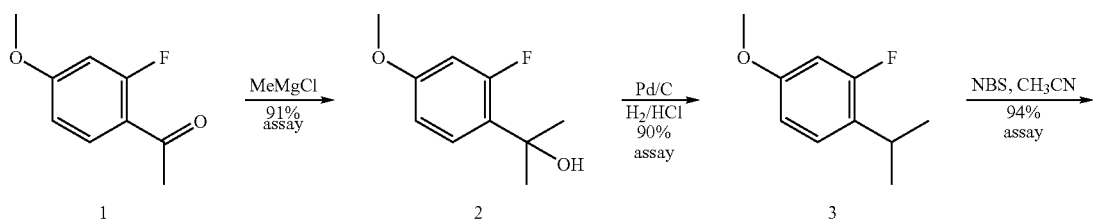

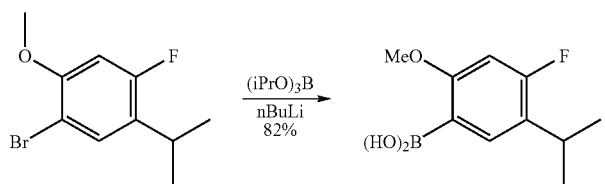

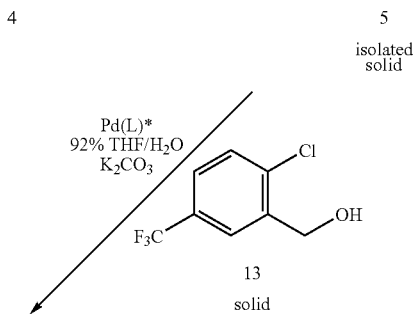

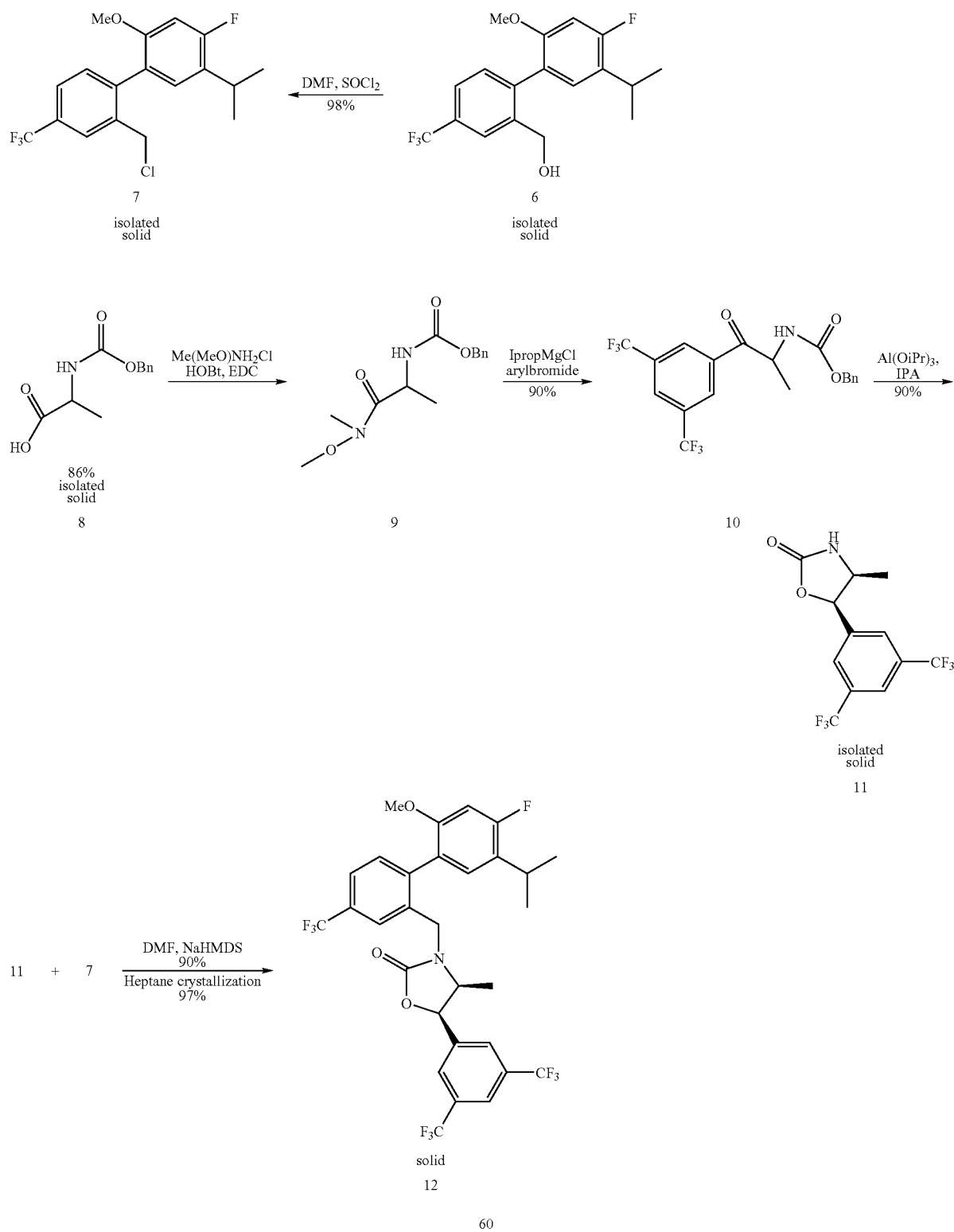

Synthesis of Intermediate 7

Intermediate 7 is made in 6 steps from readily available materials. The synthesis is summarized below as a 4-step synthesis of the boronic acid intermediate 5, which is isolated as a solid material. The boronic acid is then carried on in two more steps to the key intermediate 7, which is also isolated as a solid product.

The boronic acid intermediate is synthesized in 4 steps as shown below, and as summarized in Scheme 2. The yields are also shown in Scheme 2:

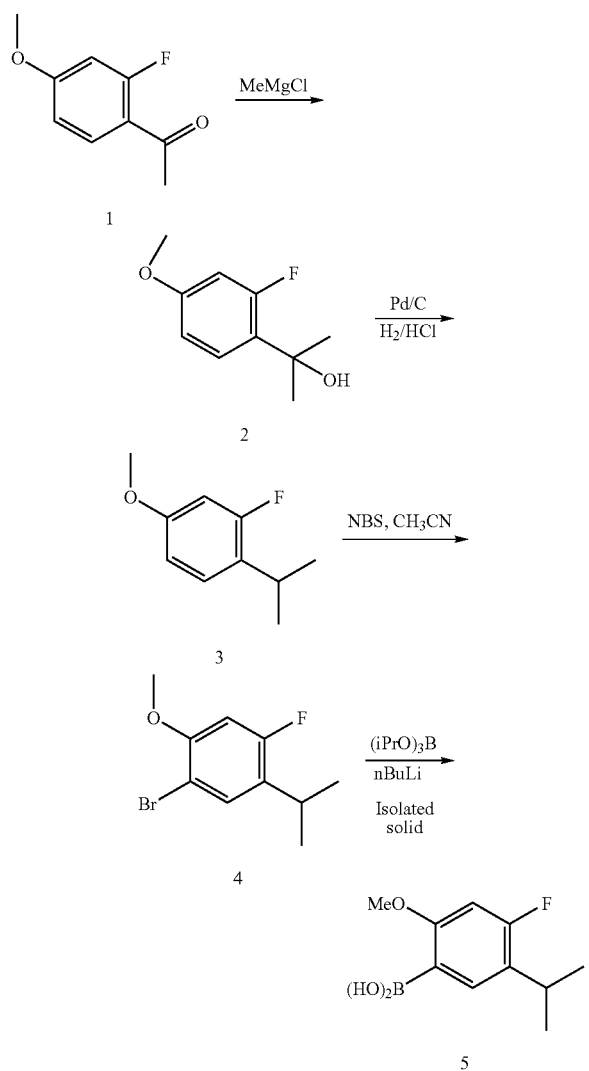

Scheme 2

Conversion of 1 to 2:

THF (24 L) was added to a 100 L cylindrical vessel at room temperature. To this was added 2.75 kg of $CeCl_3$. The resultant slurry was aged at room temperature for 1.5 hours. A sample was then examined under a microscope to confirm that the desired form change had occurred. The slurry was cooled to 9° C. and MeMgCl was added. The rate of addition was adjusted to maintain internal temperature below 19° C. The mixture was cooled to −11° C., and a solution of acetophenone 1 (4.0 kg diluted to 10 L with THF) was added dropwise, maintaining the internal temperature below 0° C. The reaction mixture was then aged at a temperature below 0° C. for an hour. The reaction was quenched with 5.7 L of 3N HCl in a dropwise fashion, maintaining the internal temperature below 15° C. The quenched reaction mixture was then aged at 5-10° C. for 1.5 hours and was filtered through a plug of Solka Floc.

Hydrogenation of 2 to 3:

The THF solution of 2 was solvent switched into ethanol (~18 L volume), and 1.9 L HCl was added, followed by 190 gm of 10% Pd/C (50% water). The mixture was placed under 15 psi hydrogen at 40° C. until the reaction was complete based on HPLC analysis. The mixture was cooled to room temperature. The catalyst was removed by filtration using Solka-Flok as a filter aid. The anisole product in ethanol was then solvent switched into acetonitrile for the next step.

Bromination of 3 to 4:

Anisole 3 is diluted in acetonitrile (1.72 L, 4 mL MeCN/mMol 3). This mixture is warmed to 35° C., and NBS (1.1 eq, 84 g) is added in a single solid addition. The reaction is maintained at 35° C. and is complete in 2-4 hours. The solution is concentrated to 400 mL total volume and diluted with 1 L of toluene. The solution is then washed with sodium thiosulfate and water to remove the succinimide by-product. The organic layer is then concentrated and solvent switched to toluene.

Conversion of Aryl Bromide 4 to Boronic Acid 5:

A 75 L glass reaction vessel was charged with 1.87 kg of aryl bromide 4 (7.6 Mol), which was added as 6.4 kg of a 29.1 wt % solution of 4 in toluene. This solution was diluted with 5.6 L of THF. The vessel was flushed with nitrogen, and tri-isopropylborate (1.35 eq, 2.35 L, 10.3 Mol) was added. The mixture was cooled to <−70° C. Then 5.9 L of 1.6 M n-BuLi in hexanes (9.5 Mol) was added slowly over 4 hours, maintaining a temperature of <−55° C. Thirty minutes after completion of the n-BuLi addition, the reaction was complete by LC analysis. The reaction was warmed to −35° C. and quenched into 3.0 M $H_2SO_4$ solution (5.6 L). The aqueous phase after the quench should be acidic (pH ~2). MTBE (7.5 L) was added to the mixture to dilute the organic layer. The mixture was stirred (15 min) and the aqueous layer was cut away. The organic layer was washed with another 5.6 L of a 3.0 M $H_2SO_4$ solution (15 min). After separating layers again, the organic MTBE/Toluene layer was extracted twice with 1 M KOH (15.1 L first and then 7.6 L). The two KOH extractions were combined, diluted with 2-propanol (6.4 L), and cooled to 15° C. Then the solution was slowly acidified to pH ~2 using 3.0 M sulphuric acid (~7.6 L) while maintaining temperature at 15-20° C. The resulting slurry was stirred for 1 h and then filtered. The filter cake was washed with water (2×6 L) and dried under an air flow for 1 day. The filtered solid was placed in an oven under vacuum at 50° C. for 2-3 days to decompose a diaryl impurity and to dry the off-white crystalline solid, which was boronic acid 5.

Boronic acid 5 is then converted to the biaryl intermediate 7 in 2 steps, which are summarized in Scheme 3 below and are described in detail in the subsequent procedures.

Scheme 3

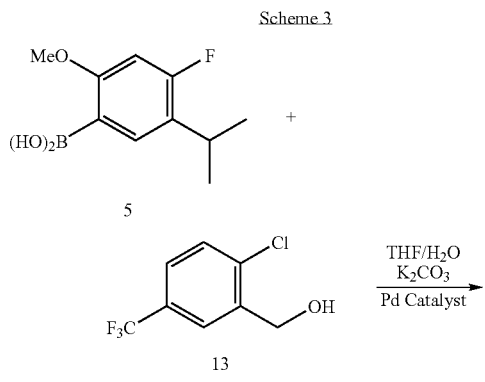

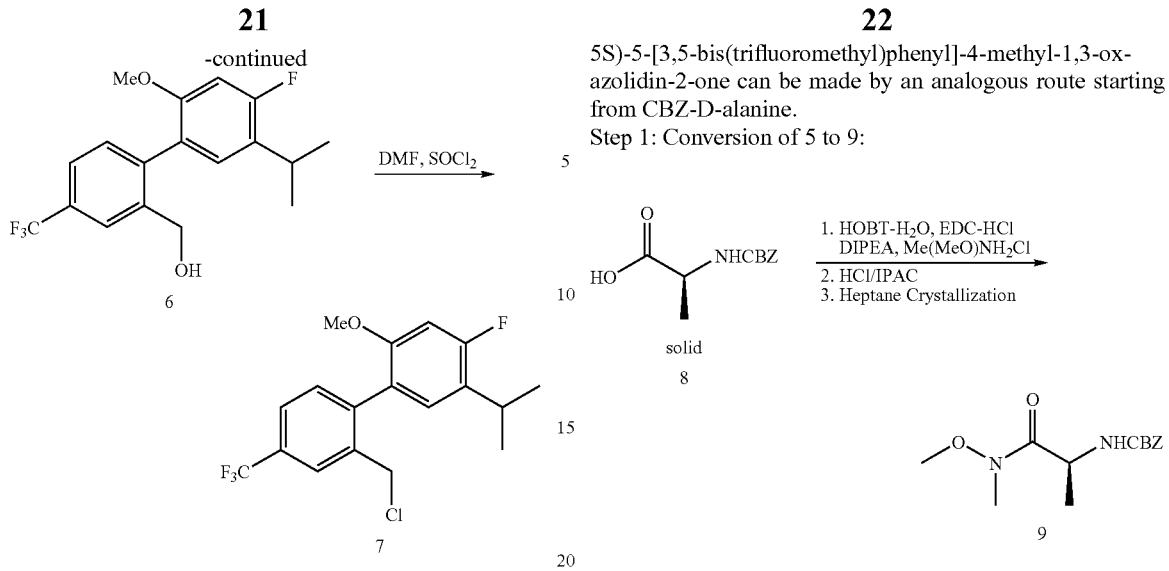

Step 1: Suzuki Coupling Reaction of Boronic Acid 5 and Aryl Chloride 13 to yield 6:

A 3 M K₂CO₃ solution is prepared by adding 4.71 kg of solid K₂CO₃ to 10.3 L water. Cooling is applied to keep the solution at 20-25° C. THF (12 L), aryl chloride 13 (2.69 kg), and boronic acid 5 (2.74 kg) are added to the K₂CO₃ followed by a 1 L THF rinse. HPLC analysis is used to confirm the 1.00/1.00 ratio of 5/13. The solution is degassed by sparging with nitrogen gas for 70 min. The catalyst, 1,1 bis(di-tert-butylphosphino)ferrocene palladium dichloride (42 g) is added as a solid and is followed by a degassed THF rinse (1.5 L). The organic layer turns dark brown immediately. The biphasic mixture is aged at 36°-40° C. with vigorous stirring. After HPLC reveals complete conversion (15-18 h), the mixture is cooled to rt and the aqueous layer is removed. To the organic layer is added heptane (25.6 L) and water (25.6 L) and the layers are cut. The organic layer is washed with water (19 L). The organic layer is treated with 680 g Darco KB-B at rt for 60 min and filtered through solka-floc with a 10% THF/Heptane rinse (~15 L). The solvent is switched to heptane (~35 L) at ~45-50° C. until <0.5 v % of THF is left. More heptane is added to bring the total volume to ~45-50 L. The solution is seeded with crystals obtained from earlier runs if no seed bed forms. The slurry is slowly cooled to rt and then to −15° C. After aging at −15° C. for 1-2 h, after LC of the supernatant shows that there will be ~2 g/l loss of the product in the supernatant, the slurry is filtered and the product is washed with cold heptane (~25 L), providing compound 6.

Step 2: Chlorination of 6 to 7:

To a solution of biaryl compound 6 (3.4 kg) in DMF (17 L) which was maintained at 10° C. was added thionyl chloride (940 ml), and then the mixture was warmed to room temperature. The mixture was aged until >99.8% conversion was measured by HPLC. Water (3.4 L) was then added. Seed crystals (1 wt %) were added, and the mixture was aged for 30 min more before slowly adding 5.1 L of additional water over ~1 hr. The solid was filtered and washed with first 20 L 1:1 DMF:water and then 3×20 L water. The solid product 7 was dried at 20° C. until <0.1 wt % water remained.

Chiral Synthesis of (4S,5R)-5-[3,5-Bis(trifluoromethyl)phenyl]-4-methyl-1,3-oxazolidin-2-one (11)

The oxazolidinone intermediate 11 is made directly from the chiral starting material CBZ-L-alanine (8) by the 3-step route shown below. The enantiomer of this compound (4R, 5S)-5-[3,5-bis(trifluoromethyl)phenyl]-4-methyl-1,3-oxazolidin-2-one can be made by an analogous route starting from CBZ-D-alanine.

Step 1: Conversion of 5 to 9:

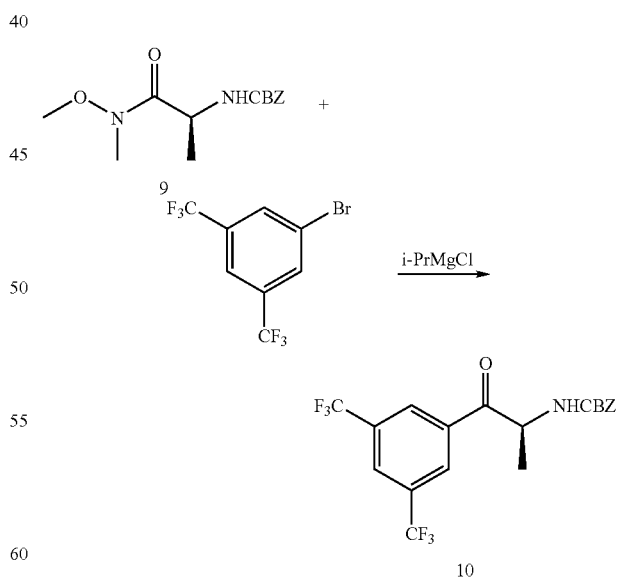

CBZ-L-Alanine (6.5 kg, 28.5 mol), HOBT-hydrate (4.8 kg, 34.8 mol), Weinreb amine-HCl salt (3.4 kg, 36.2 mol) and THF (32 L) are charged to a clean flask under nitrogen. The mixture is cooled to 0-10° C. and then DIPEA (12.4 L) is slowly added at a temperature less than 25° C. EDC-HCl (7 Kg, 36.2 mol) is then added slowly with cooling at 15°-25° C. The slurry is aged overnight at 20°-25° C. The mixture is then cooled to 0°-10° C., and 3 N HCl (12 L) is added slowly. Then IPAC (32 L) is added and the layers are separated. The organic layer is washed once with HCl (13 L) and twice with 8% NaHCO₃ (13 L) (CAUTION: FOAMING). The organic layer is then concentrated under vacuum to about 15 L at 50° C. The clear solution is cooled slowly to room temperature, allowing the product to crystallize. Heptane (~70 L) is then added slowly. The slurry is filtered, washed with heptane (18 L), and dried at room temperature on the filter pot. Product is obtained with >99.9% ee measured by chiral HPLC.

Step 2: Conversion of 9 to 10

The Weinreb amide 9 from the previous step (6 kg, 22.5 mol) and 3,5-bis(trifluoromethyl)bromobenzene (4.85 L, 28.1 mol) are dissolved in anhydrous THF (24 L). The solution is purged with nitrogen to remove oxygen. The water content should be <500 ppm at this point. Atmospheric distillation can be carried out to azeotropically remove water if necessary. The solution is cooled to −10° C. and iso-PrMgCl in THF (56.4 mol) is slowly added (2 hours) to the reaction via addition funnel, maintaining a reaction temperature ≦−5° C. The solution is allowed to warm to 20° C. and aged overnight at 20° C., until the amide is <0.5 LCAP. The reaction is then cooled to −10° C. under nitrogen and is quenched slowly over 2 hours into 5N HCl (14 L) that is maintained at 0-5° C. MTBE (12 L) is added and the biphasic mixture is agitated for 5 min. After warming to 20°-25° C., it is allowed to settle for 30 min, and then the layers are separated. The organic layer is washed with water twice (12 L The organic layer is vacuum transferred through a 1-micron in-line PTFE filter into a distillation flask and is then concentrated to ~12 L under vacuum (internal temperature <40° C.) to a minimum agitated volume. The solution is then azeotropically dried with toluene and taken to a minimum agitated volume again. The solution containing ketone 10 is used directly in the next step.

Step 3: Reduction of Ketone 10 to Chiral Oxazolidinone 11:

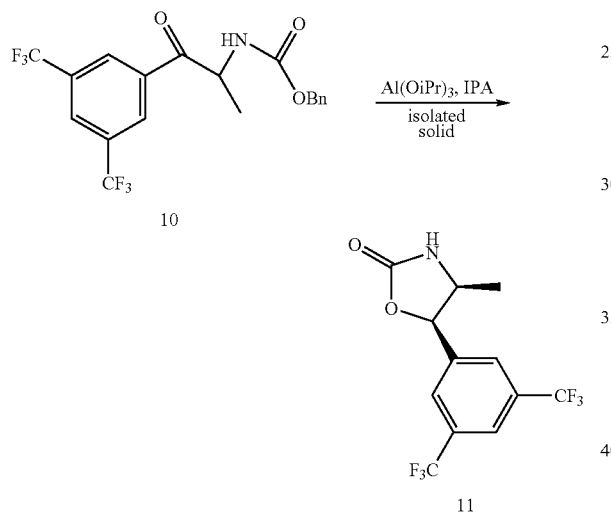

The ketone 10 (6 kg) is heated at 50° C. with 0.3 eq of Al(O-i-Pr)₃ (790 g) in 12 L IPA and 18 L of toluene for 15.5 hours. The solution is cooled to ambient temperature, and solid KOH pellets (1.35 kg) are added slowly with vigorous stirring, while keeping the temperature at <25° C. After about 2 hours, when HPLC shows >99.5% cyclization, 33 L of 1N HCl solution is added to quench the reaction, which is kept at <25° C. If a rag layer of solids forms, it should be filtered off. The rag layer is racemic oxazolidinone, and removal increases the enantiomeric excess. The organic layer is then washed first with 36 L of 0.5N HCl, then with 6 L IPA combined with 45 L water, and finally with 6 L IPA combined with 36 L water. The organic layer is transferred via an inline filter. The solvent is switched to heptane (target volume is ~42 L) at ~40° C. until <2 v % toluene is left. Aging at rt for 2 h gives the solid product 11.

Alkylation of Oxazolidinone 11 with 7

Oxazolidinone 11 is alkylated with 7 to yield the desired product, (4S,5R)-5-[3,5-bis(trifluoromethyl)phenyl]-3-{[4'-fluoro-5'-isopropyl-2'-methoxy-4-(trifluoromethyl)biphenyl-2-yl]methyl}-4-methyl-1,3-oxazolidin-2-one (12):

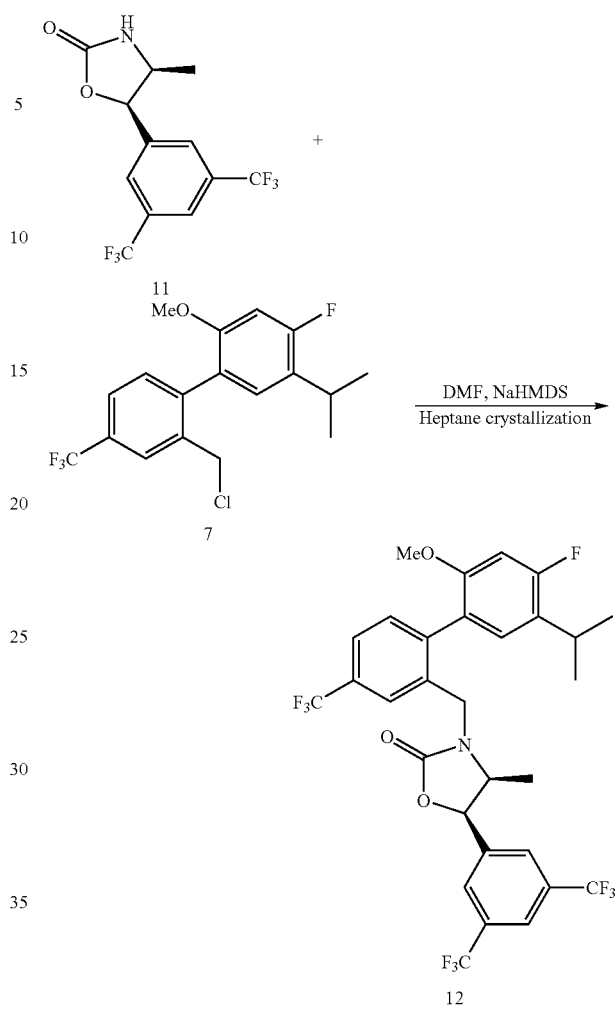

The chiral intermediate (4S,5R)-5-[3,5-Bis(trifluoromethyl)phenyl]-4-methyl-1,3-oxazolidin-2-one (11) which was made above is dissolved in DMF (2.8 kg in 32.7 L) and cooled to −15° C. 2.0 M NaHMDS (3.92 L, 1.05 eq) was then added over 1.5 hr, followed by addition of the biaryl chloride 7 (2.8 kg) in DMF. The mixture was warmed to +12° C. and was aged until complete conversion took place. Then 5N HCl (3.4 L) was added, followed by 16 L of 10% IPAC/Heptane and 34 L of water, keeping the temperature between 10° C. and 20° C. throughout. The layers were cut and the organic layer was washed twice with 14 L of 1:1 DMF:water followed by two 14 L water washes. The organic layer was assayed for yield and was then filtered through 2.4 kg of silica gel to remove the excess oxazolidinone to <0.5%. The silica was washed with 5% IPAC/Heptane. The combined organic solutions were distilled to remove IPAC to <1%. The warm heptane solution was then transferred slowly into a 20° C. heptane solution containing 10 wt % seed. The slurry was then cooled to −20° C. and filtered. The filter cake was washed with cold heptane and was then dried, yielding the desired product 12.

EXAMPLES

The following examples are provided to more fully illustrate the invention and are not to be construed as limiting the scope of the invention, which is defined by the appended claims.

Examples of preparations of pharmaceutical formulations are provided below. Bioavailability is determined in vivo by dosing trial formulations and/or other formulations of the active pharmaceutical ingredient (API) to Rhesus monkeys (normally three monkeys per trial) at a dose of 1 mg/kg of the API and then measuring the amount of API in the serum or blood as a function of time. Comparisons are made with other formulations containing the same amount and same concentration of the API, such as a solid formulation with conventional excipients or a liquid filled gelatin capsule containing equal parts by weight of Tween 80 and Cremophor EL and varying amounts of the API. The API is any compound of Formula I to Ij, and most often is Compound H.

Dissolution of the formulations in water or simulated gastric fluid can be observed and measured to determine the concentration and rate of dissolution of the active CETP inhibitor in the fluid using the formulations of this invention or other formulations, including formulations with conventional excipients as controls to determine the improvements in dissolution using the formulations of this invention.

Example 1

Spray Dry Formulation

Formulation 1:
The spray dried formulations comprise compound II (10-20% w/w); an optional surfactant, such as (1) 2-4% SDS (sodium dodecyl sulfate), (2) 5% Vitamin E TPGS, (3) 2% Tween 80, (4) 2% Span 80, or (5) 2% Cremophor EL, or a mixture of two or more of these surfactants; and the balance is HPMCAS-L (purchased as AQOAT from Shin Etsu). The components are dissolved or suspended in acetone or methanol (0.5-18% w/v solids), and then spray dried as described below.
Formulation 2:
The spray dried formulation comprises compound II (20% w/w); 10% SDS (sodium dodecyl sulfate); and the balance is copovidone (purchased as Kollidon VA64 from BASF). The components are dissolved or suspended in methanol (0.5% w/v solids), and then spray dried as described below.
Formulation 3:
The spray dried formulation comprises compound II (10% w/w); 2% SDS (sodium dodecyl sulfate); and the balance is hypromellose phthalate (purchased as HPMCP from Shin Etsu). The components are dissolved or suspended in acetone (1% w/v solids), and then spray dried as described below.
Formulation 4:
The spray dried formulations comprise compound II (10% w/w); 5-10% Vitamin E TPGS; and the balance is hypromellose (purchased as HPMC from Shin Etsu). The components are dissolved or suspended in methanol (1-10% w/v solids), and then spray dried as described below.
Solution Preparation:
Compound II, optional surfactant or surfactants, and polymer are mixed with acetone or methanol as follows, yielding a solution (which may be a structured suspension). The polymer is dissolved in the solvent before the other ingredients are added. The polymer is slow to dissolve and is added to the solvent over an extended period of time with vigorous stirring, such as by using a high shear mixer or magnetic stir bar and stir plate. After the polymer has dissolved in the solvent (based on visual appearance; may be hazy or cloudy), it is stirred for a period of at least one more hour. The surfactant is then dissolved in the polymer solution/suspension in a similar manner, and the drug is added last. The surfactant and drug dissolve completely. The resulting solution/suspension is stirred for at least an additional 30 min prior to spray drying.
Spray Drying Process 1:
Spray drying is carried out in a Niro SD Micro spray drier. Heated dry nitrogen and formulation solution are fed concurrently into a two-fluid nozzle (30° angle) and are then discharged as a spray into the drying chamber, along with additional heated gas, resulting in rapid evaporation to form particles. The dried particles are carried by the processing gas into a cyclone and then into a bag filter chamber for collection. Three processing rates are controlled and monitored: 1) solution feed rate, 2) processing nitrogen flow rate, and 3) atomizing nitrogen flow rate. The solution feed rate is controlled by an external peristaltic pump, and is ~5-20 ml/min on a laboratory scale. The atomizing nitrogen rate and processing nitrogen rates are 2-3 kg/hr for atomizing nitrogen and 20-30 kg/hr for processing nitrogen. The targeted processing gas temperature at the drying chamber outlet is at or slightly below the boiling point of the solvent, although temperatures in the range of 44 to 70° C. have been demonstrated to be adequate, and the inlet chamber temperature (at the outlet of the nozzle) is adjusted to obtain the desired outlet temperature. An inlet temperature setpoint of 80-90° C. is typical. Residual solvent levels in the product are typically low (<1% w/w).
Spray Drying Process 2:
Processing configuration is similar to Process 1, except that spray drying is carried out in a Niro PSD-1 extended chamber spray drier equipped with a two-fluid nozzle with 1 mm orifice. The following processing conditions are controlled or monitored: formulation solution feed rate (2-7.6 kg/hr), processing gas flow rate (35-38 mm $H_2O$), atomization ratio (ratio of atomization gas flow rate to feed rate) (0.9-2.8), atomization pressure (0.25-1.5 bar), outlet gas temperature (43-70° C.), and inlet gas temperature (61-134° C.).
Post Spray Drying Processing:
At the smaller processing scale, material collection occurs in two areas, the cyclone and the bag filter chambers. Typical mean particle sizes resulting from the Spray Drying Process 1 range from 1 to 30 μm, with individual particles measuring between <1 μm and >100 μm, as sampled from the cyclone collection area. The majority of particles in the bag filter are 1 μm or less, although the particles are highly agglomerated. Under Spray Drying Process 2 conditions, particles are harvested from the cyclone collection chamber only, and the typical mean particle size may be much larger, typically ranging between 5 to 70 μm.

The spray dried particles are made into granules as follows. The particles are blended in a suitable blender (V or Bohle) with microcrystalline cellulose such as Avicel (a filler), lactose (a filler), croscarmellose sodium (a disintegrant), and magnesium stearate (a lubricant). The blended powders are then roller compacted into granules, subjected to extragranular lubrication, and filled into capsules.

A formulation as described above comprised of 8.8% (w/w) Compound II, 35.2% HPMCAS-LF, 25.75% lactose monohydrate, 25.75% microcrystalline cellulose (Avicel PH 102), 3% croscarmellose sodium, 0.5% colloidal silicon dioxide, and 1% magnesium stearate was transferred to capsules (568 mg fill weight), with each capsule containing 5 mg of Compound H. The pharmacokinetic profile of this composition was tested in a panel of 3 fasted Rhesus monkeys with a single dose of 1 mg/kg. The pharmacokinetic measurements of Compound II in the blood for a period of 24 hours are as follows: $AUC_{0-24}$ is 1.99±1.10 μM*hr; $C_{max}$ is 0.12±0.08 μM; and $T_{max}$ is 6.7±2.3 hr.

For comparison, a formulation containing Compound II without the polymer was made and tested, as follows. The non-polymer formulation contained 5% of Compound II, 5% SDS surfactant, 1.5% HPC-EXF, 1% croscarmellose sodium, and 87.5% lactose, and was prepared by wet granulation and used in a dry-filled capsule. The pharmacokinetic profile of this composition was measured by administering a single 1 mg/kg dose to a panel of 3 fasted Rhesus monkeys and then measuring the amount of Compound II in the blood of the monkeys for a period of at least 24 hours. The pharmacokinetic data are as follows: $AUC_{0-24}$ is 0.67±0.0.32 µM*hr, $C_{max}$ is 0.04±0.03 µM, and $T_{max}$ is 18.7±9.2 hr. The pharmacokinetics are not as good for the "conventional" formulation as for the polymer formulations, even though the "conventional" formulation used as a control included a surfactant.

In general, formulations of HPMCAS with the API and an optional surfactant comprise 4%-30% API and 0-12% surfactant, with the balance of the formulation being HPMCAS.

Example 2

Hot Melt Extrusion

The following two formulations were made by hot melt extrusion. Amounts are expressed as weight %. Kollidon VA64 is a copolymer of polyvinylpyrrolidinone and polyvinyl acetate having a comonomer ratio of about 1.2:1. It is also known as copovidone. It has a glass transition temperature ($T_g$) of about 110° C., and melts at about 140° C. Each formulation was made on a 200 g scale:
(1) Compound II, 30%; Vitamin E TPGS, 15%; Kollidon VA64, 55%.
(2) Compound II, 20%; Tween 80, 1.5%; Span 80, 1.5%; Cremophor EL, 1.5%; Kollidon VA64, 75.5%.
Formulation 1

Formulation 1 was made by first making a pre-extrusion blend, which is a granulated mixture of the ingredients, and then feeding the granulated mixture into a twin screw extruder. The granulated mixture was made by combining the Kollidon VA64 polymer and Compound II at room temperature in a Bohle BMG granulator equipped with a No. 4 bowl (2 L), and then adding molten Vitamin E TPGS dropwise as the granulating fluid to the mixture as it was being stirred in the granulator. The Vitamin E TPGS was heated to somewhat above the melting temperature of about 40° C. so that it could be added as a liquid. The chopper speed was 1000 rpm, and the impellor speed was 400 rpm.

The pre-extrusion blend was fed into a Thermo Prism 16 mm L/D 40:1 Hot Melt Twin Screw Extruder. The barrel of the extruder has 10 temperature zones numbered 1-10, with Zone 1 at the entry end of the barrel and Zone 10 just before the die. Zone 1 is not heated and has no temperature measurement. Zones 2-10 each have temperature control, and the temperatures of each of these zones can be measured. The temperature of the die is not controlled but can be measured. The feed was introduced into Zone 2 through a feed throat. The screws were set so that mixing occurred in two places, across Zones 6 and 7 and again across Zones 8 and 9. The mixing ended immediately past the vent port. The granulated pre-extrusion mixture was fed into the feed port of the extruder at about 10 g/min from a K-Tron feeder. The screw speed was 100 rpm.

The profile of temperature set points in the extruder for Zones 2-10 was: Zones 2-5, 20° C.; Zones 6-10, 130° C. The actual temperatures in these zones were: Zones 2-3, 22-23° C.; Zone 4, 28° C.; Zone 5, 48° C.; Zones 6-9, 130° C.; Zone 10, 133° C. Zone 10 was initially set at 150° C. to avoid pressure during startup, and then the temperature set point was lowered to 130° C. once the extrusion began. The temperature of the molten polymer exiting from the die was 107-108° C. There was no appreciable buildup of die pressure. The extrudate was clear, and it appeared homogeneous.

The solid extruded polymer was then milled using a Fitz Mill with a knife configuration, Impact forward, with a 1722-0033 screen at 7500 rpm.
Formulation 2

Formulation 2 was made using the same procedure as was used for Formulation 1, except that when the pre-extrusion blend was made, the three surfactants were each added dropwise separately to the granulator while stirring of the granulated mixture continued. The Span 80 and Tween 80 are liquids at room temperature and therefore were not heated before they were added to the mixture that was being stirred in the granulator.

The extrusion was carried out under the same general conditions as the extrusion of Formulation 1. The only change is that the temperature of Zone 10 was set at 145° C. The temperature of the molten extrudate as it exited from the die was 121-125° C. The die pressure was 1-5 bar. The extrudate was milled using the same method as was used for Formulation 1.

Example 3

Formulation for Tablets by HME

The compositions of three formulations for making tablets containing 12%, 10%, and 8% of Compound II are shown in the following table. The last 3 rows summarize pharmacokinetic data obtained by administering a single dose of the formulation at a dose of 1 mg/kg to panels of 3 fasted Rhesus monkeys and measuring the concentration of Compound II in the blood for a period of at least 24 hours. The compositions can be varied more broadly to obtain desired properties, as summarized after the table.

| Component | Amount (wt % of total formulation) | | |
|---|---|---|---|
| Compound II | 12% | 10% | 8% |
| Copovidone | 42% | 35% | 28% |
| Vitamin E TPGS | 6% | 5% | 4% |
| Microcrystalline cellulose (filler) | 22.16% | 29% | 35.7% |
| Lactose (filler) | 11.08% | 14.5% | 17.8% |
| Croscarmellose sodium (disintegrant | 6% | 6% | 6% |
| Magnesium stearate (lubricant) | 0.5% | 0.5% | 0.5% |
| Colloidal silicon dioxide* (glidant) | 0.25% | 0.25% | 0.25% |
| AUC (0-24 hrs) | 2.29 ± 0.21 | 1.62 ± 0.27 | 1.73 ± 0.28 |
| $C_{max}$ (µM × hr) | 0.13 ± 0.01 | 0.10 ± 0.01 | 0.10 ± 0.01 |
| $T_{max}$ (hrs) | 6.7 ± 1.2 | 5.3 ± 2.0 | 4.0 ± 2.0 |

Representative ranges of the amounts of the components that can be used and their function are as follows: API, 0.5-15%; copovidone (HME polymer), 2-60%; Vitamin E TPGS (surfactant), 0.25-10%; microcrystalline cellulose (filler), 5-95%; lactose (filler), 5-95%; croscarmellose sodium (disintegrant), 1-15%; magnesium stearate (lubricant), 0.1-2%; and colloidal silicon dioxide (glidant), 0-1%. Colloidal silicon dioxide surprisingly increased the tensile strength of the tablet without affecting the disintegration time. Representative ranges of the amounts of API, copovidone, and Vitamin E TPGS are 1-35%, 5-90%, and 0.5-25% respectively.

Substitutes for the polymers and excipients described above include, but are not limited to, the following polymers and excipients. In particular, where a trade name or brand name is used, the same materials having other brand or trade names are also included: HME polymer—Eudragits (acrylate-methacrylate copolymers), PVP, HPC, HPMC, HPMCP, HPMCAS, CAS, CAP, and CAT; Surfactants—SDS, Cremophors (various grades), polysorbates (various grades), Solutol, Gelucires, Spans (various grades), PEG's; fillers—dicalcium phosphate, silicified microcrystalline cellulose, starch, mannitol; disintegrants—crospovidone, sodium starch glycolate, calcium silicate, starch; optional colorants—red iron oxide, yellow iron oxide, black iron oxide, titanium dioxide, FD&C Blue #2; and optional coating—Opadry I, Opadry II, Opadry II HP.

The formulations in the table above are made by hot melt extrusion by the following procedure. Compound II is fed using a Ktron K20 twin screw powder feeder at extruder barrel zone 1 through the top feed port of the barrel section (2 kg/hr). Polymer (Kollidon VA64) is fed using a Ktron K20 twin screw powder feeder at extruder barrel zone 2 through a twin screw Leistritz side stuffer with top vent port in the barrel section (7 Kg/hr). Molten Vitamin E TPGS is fed using a Zenith gear pump through heated stainless steel lines using a coriolis meter to determine in-line flow rate and a pressure gauge to assess liquid feed stability (also for safety) together with an in-line temperature probe. The liquid is pumped into the extruder through a standard Liestritz liquid injection nozzle in the top of barrel zone 3 using a 0.5 mm diameter nozzle. The liquid is injected at ca. 100° C. and 1 kg/hr.

A vent (or two vents) are located at barrel zones 7, 8, and/or 9. These are ambiently vented to remove water vapor. The remaining barrel sections are closed. All feeders are placed on load cells to continuously monitor changes in weight. The barrel temperature is at room temperature at zone 1, and the temperatures are at about 130° C. at Zone 3 or 4. Zones 5-10 are heated to about 130° C.

A custom die adapter is used to enable in-line transmission of NIR and Raman measurements so that the drug concentration, TPGS concentration, and, potentially, the product quality and other attributes can be measured continuously on-line. A four hole strand die is used to extrude material onto a chilled roll unit made by ThermoElectron. The chilled roll unit uses cool water to produce a brittle sheet of extrudate that is subsequently chopped up into particles by a "kibbler" (basically a rotor with perpendicular pegs that wacks at the brittle sheet that is conveyed to the rotor).

The screw design of the extruder is basically 1.5 D pitch forward conveying fully intermeshing elements for the first 3-4 zones followed by a long single mixing zone consisting of 10 forward 30 degree mixing paddles, 10 forward 60 degree mixing paddles, and 25 90 degree mixing paddles. After this mixing zone there is a simple conveying section consisting of primarily 1 D pitch fully intermeshing elements.

The particles from the kibbler above are milled using a Fitz mill prior to downstream processing/tabletting. The milled extrudate is then blended in a suitable blender (V or Tote) with microcrystalline cellulose (e.g. Avicel) (a filler), lactose (a filler), croscarmellose sodium (a disintegrant), and colloidal silica (a glidant). Colloidal silica may be sieved alone or co-sieved with the fillers prior to blending.

The blend is then lubricated with magnesium stearate. The lubricated blend is compressed into tablets. The compressed tablets may optionally be coated.

Example 4

A formulation for a 100 mg tablet using spray dried HPMCAS as described in Example 1 is shown below:

| mg Per Unit (Tablet) | Ingredient | Weight Percent |
|---|---|---|
| 100.0 | Compound II | 15.0 |
| 400.0 | HPMCAS | 60.0 |
| 115.0 | Lactose, Monohydrate | 17.3 |
| 40.0 | Croscarmellose sodium | 6.0 |
| 5.0 | Silicon dioxide, Colloidal | 0.75 |
| 6.7 | Magnesium Stearate | 1.0 |
| 666.7 mg per unit (tablet) | | 100.0 |

A formulation for a 150 mg tablet using spray dried HPMCAS as described in Example 1 is shown below:

| mg Per Unit (Tablet) | Ingredient | Weight Percent |
|---|---|---|
| 150.0 | Compound II | 15.0 |
| 600.0 | HPMCAS | 60.0 |
| 172.5 | Lactose, Monohydrate | 17.3 |
| 60.0 | Croscarmellose sodiuml | 6.0 |
| 7.5 | Silicon dioxide, Colloidal | 0.75 |
| 10.0 | Magnesium Stearate | 1.0 |
| 1000.0 mg per unit (tablet) | | 100.0 |

What is claimed is:
1. A pharmaceutical composition comprising:
(a) a CETP inhibiting compound having formula Ii, or a pharmaceutically acceptable salt thereof:

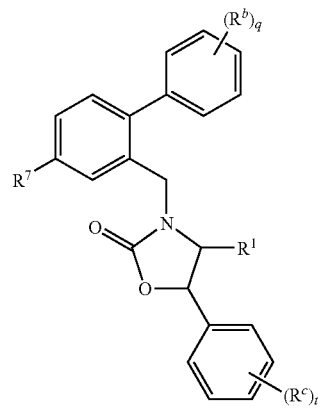

wherein $R^1$ is selected from the group consisting of H and —$C_1$-$C_2$ alkyl;
$R^7$ is selected from the group consisting of Cl and —$CF_3$,
Each $R^b$ is independently selected from the group consisting of —$C_1$-$C_3$ alkyl, —$OCH_3$, and F;
Each $R^c$ is independently selected from the group consisting of halogen, —$CH_3$—$CF_3$, and —CN;
q is 2 or 3; and
t is an integer from 0-2;
(b) a concentration-enhancing polymer selected from the group consisting of hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, polyvinylpyrrolidinone, and polyvinylpyrrolidinone-polyvinylacetate copolymers; and (c) optionally one or more surfactants selected from the group consisting of sodium dodecyl sulfate and one or more nonionic surfactants selected from (a) sorbitan fatty acid esters, (b) polyoxyethylene sorbitan fatty acid esters, (c) polyoxyethylene castor oils, (d) polyoxyethylene hydrogenated castor oils, and (e) vitamin E TPGS; and mixtures thereof.

2. The pharmaceutical composition of claim 1, wherein said concentration-enhancing polymer is selected from the group consisting of hydroxypropyl methyl cellulose acetate succinate (HPMCAS), hydroxypropyl methyl cellulose phthalate (HPMCP), cellulose acetate phthalate (CAP), and cellulose acetate trimellitate (CAT).

3. The pharmaceutical composition of claim 2, wherein said composition is made by the spray drying of a solution comprising the compound of formula II or a pharmaceutically acceptable salt thereof, the concentration-enhancing polymer, the optional one or more surfactants, and one or more solvents.

4. The pharmaceutical composition of claim 3, wherein said concentration-enhancing polymer is hydroxypropyl methyl cellulose acetate succinate (HPMCAS).

5. The pharmaceutical composition of claim 4, which comprises 4-30% of compound II and 0-12% surfactant, with the balance of the composition being HPMCAS.

6. A pharmaceutical composition, which comprises HPMCAS and 4-30% of compound II, wherein compound II has the formula:

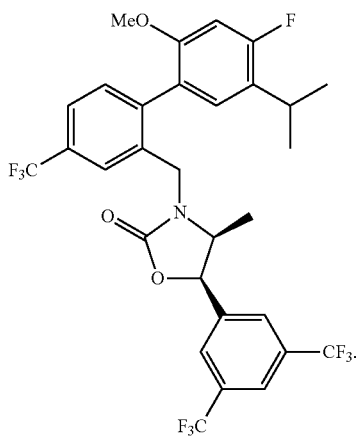

7. The pharmaceutical composition of claim 1, wherein said concentration-enhancing polymer is selected from polyvinylpyrrolidinone and polyvinylpyrrolidinone-polyvinylacetate copolymer.

8. The pharmaceutical composition of claim 7, wherein said concentration-enhancing polymer is a polyvinylpyrrolidinone-polyvinylacetate copolymer.

9. The pharmaceutical composition of claim 8, wherein said surfactant is vitamin E TPGS and said polyvinylpyrrolidinone-polyvinylacetate copolymer is copovidone.

10. A pharmaceutical composition, which comprises the compound of formula II, copovidone, and vitamin E TPGS, wherein the compound of Formula II has the structure

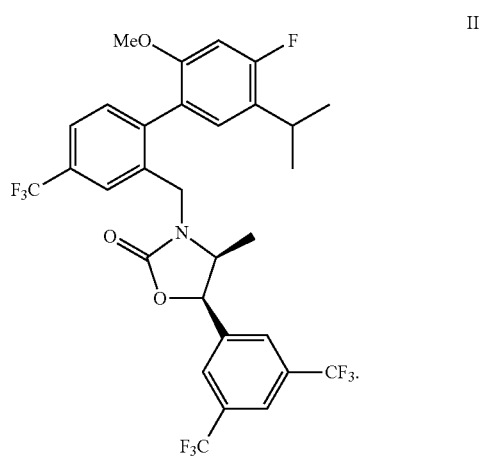

11. The pharmaceutical composition of claim 10, wherein said composition is made by hot melt extrusion of a mixture comprising the compound of formula II or a pharmaceutically acceptable salt thereof, copovidone, and vitamin E TPGS to yield an extrudate, which is subsequently milled and blended with excipients.

12. The pharmaceutical composition of claim 11, wherein the extrudate comprises 1-35 wt% of compound II, 5-90% of copovidone, and 0.5-25% of vitamin E TPGS.

13. The pharmaceutical composition of claim 10, which comprises 0.5-15% of the compound of formula II, 2-60% copovidone, 0.25-10% vitamin E TPGS, 5-95% microcrystalline cellulose (filler), 5-95% lactose (filler), 1-15% croscarmellose sodium (disintegrant), 0.1-2% magnesium stearate (lubricant), and 0-1% colloidal silicon dioxide (glidant).

14. A pharmaceutical composition in the form of a tablet comprising 0.5-15% compound II, 2-60% copovidone, 0.25-10% vitamin E TPGS, 5-95% microcrystalline cellulose (filler), 5-95% lactose (filler), 1-15% croscarmellose sodium (disintegrant), 0.1-2% magnesium stearate (lubricant), and 0-1% colloidal silicon dioxide (glidant), wherein the tablet is made by compressing the composition of claim 13.

15. A pharmaceutical composition in the form of a tablet comprising 8-12% compound II, 28-42% copovidone, and 4-6% vitamin E TPGS, wherein the tablet is made by compressing a composition of claim 13 which comprises 8-12% compound II, 28-42% copovidone, and 4-6% vitamin E TPGS.

* * * * *